(12) United States Patent
Kraus et al.

(10) Patent No.: US 7,688,069 B2
(45) Date of Patent: Mar. 30, 2010

(54) ULTRA-LOW FIELD NUCLEAR MAGNETIC RESONANCE AND MAGNETIC RESONANCE IMAGING TO DISCRIMINATE AND IDENTIFY MATERIALS

(75) Inventors: Robert H. Kraus, Los Alamos, NM (US); Andrei N. Matlashov, Los Alamos, NM (US); Michelle A. Espy, Los Alamos, NM (US); Petr L. Volegov, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 45 days.

(21) Appl. No.: 11/804,799

(22) Filed: May 18, 2007

(65) Prior Publication Data

US 2008/0284433 A1 Nov. 20, 2008

(51) Int. Cl.
*G01V 3/00* (2006.01)
(52) U.S. Cl. .................................. 324/309; 324/300
(58) Field of Classification Search .......... 324/300–322
See application file for complete search history.

(56) References Cited

U.S. PATENT DOCUMENTS

| | | | | |
|---|---|---|---|---|
| 7,059,524 | B2* | 6/2006 | Knowles et al. | 235/462.01 |
| 7,061,237 | B2* | 6/2006 | Pines et al. | 324/304 |
| 7,251,310 | B2* | 7/2007 | Smith | 378/57 |
| 7,394,250 | B2* | 7/2008 | Itozaki et al. | 324/300 |
| 7,397,241 | B2* | 7/2008 | Gauthausen et al. | 324/307 |
| 7,541,806 | B2* | 6/2009 | Appelt et al. | 324/303 |
| 2005/0270026 | A1 | 12/2005 | Guthausen et al. | |
| 2006/0273786 | A1* | 12/2006 | Smith et al. | 324/300 |
| 2008/0074113 | A1* | 3/2008 | Clarke et al. | 324/309 |

OTHER PUBLICATIONS

Instrumentation for Simultaneous Detection of Low Field NMR and Biomagnetic Signals; A.N. Matlachov, P.L. Volegov, M.A. Espy; R. Stolz, L. Fritzsch, V. Zakosarenko, H. Meyer, R.H. Kraus, Jr.; Squid Detected NMR in Microtesla Magnetic Fields, A. N. Matlachov, P.L. Volegov, M.A. Espy, J.S. George, R.H. Kraus, Jr.; www.elsevier.com/locate/jmr; Journal of Magnetic Resonance 170 (2007) 1-7 Ultra-low Field NMR Measurements of Liquids and Gases with Short Relaxation Times; P.L. Volegov, A.N. Matlachov, R.H. Kraus Jr.; www.sciencefirect.com; Journal of Magnetic Resonance 183 (2006) 134-141. Ultra-Low Field Nuclear Magnetic Resonance Detection of Explosives in Airport Baggage; R.H. Kraus Jr, Ph.D.; Los Alamos National Laboratory, Physics Division; Dec. 15, 2006.
PCT—Notification of Transmittal of The International Search Report and the Written Opinion of the International Searching Authority, or the Declaration, Date of Mailing Dec. 31, 2008.

* cited by examiner

*Primary Examiner*—Brij B Shrivastav
(74) *Attorney, Agent, or Firm*—Richard H. Krukar; Kermit D. Lopez; Luis M. Ortiz

(57) ABSTRACT

An ultra-low magnetic field NMR system can non-invasively examine containers. Database matching techniques can then identify hazardous materials within the containers. Ultra-low field NMR systems are ideal for this purpose because they do not require large powerful magnets and because they can examine materials enclosed in conductive shells such as lead shells. The NMR examination technique can be combined with ultra-low field NMR imaging, where an NMR image is obtained and analyzed to identify target volumes. Spatial sensitivity encoding can also be used to identify target volumes. After the target volumes are identified the NMR measurement technique can be used to identify their contents.

19 Claims, 4 Drawing Sheets

ULTRA-LOW FIELD NUCLEAR MAGNETIC RESONANCE AND MAGNETIC RESONANCE IMAGING TO DISCRIMINATE AND IDENTIFY MATERIALS

STATEMENT REGARDING FEDERAL RIGHTS

This invention was made with government support under U.S. Department of Energy Contract No. DE-AC52-06NA25396 awarded by the U.S. Department of Energy. The government has certain rights in the invention.

TECHNICAL FIELD

Embodiments relate to the fields of magnetic resonance imaging (MRI), nuclear magnetic resonance (NMR), magnetometers, magnetic gradiometers, and superconducting quantum interference devices (SQUIDs). Embodiments also relate to the fields of security, inspection, non-invasive searching, hazardous materials, explosives, and explosive precursors. Embodiments additionally relate to the fields of pattern recognition and image processing.

BACKGROUND

Nuclear magnetic resonance (NMR) techniques have been used to investigate and measure material properties. Perhaps the best known application of NMR techniques is magnetic resonance imaging (MRI) that non-invasively examines a person's body. MRI can produce three dimensional volume representations that can be displayed as two dimensional images for a diagnostician. The most common NMR instruments use very large superconducting magnets that produce intense magnetic fields.

More recently, ultra-low magnetic field NMR techniques using SQUIDs have been developed. The advantage of ultra-low magnetic fields is that they can be produced by smaller magnets. In some cases, the earth's magnetic field can be used as the measurement field.

Border security, airport security, and inspections at the entrances to secured areas have become valued, yet intrusive, aspects of life. In general, less intrusive and time consuming searches are acceptable by the public. However, only detailed searches can identify many threats. X-ray techniques and chemical sniffer techniques followed by detailed searches as required have been used in many high throughput scenarios. Regardless, many threats can easily evade detection. For example, materials such as shampoo and soap are hard to distinguish from certain explosives unless the materials are individually accessed and examined. As such, systems and methods are needed that can detect hazardous materials such as explosives and explosive precursors in a high throughput and non-invasive way.

BRIEF SUMMARY

The following summary is provided to facilitate an understanding of some of the innovative features unique to the embodiments and is not intended to be a full description. A full appreciation of the various aspects of the embodiments can be gained by taking the entire specification, claims, drawings, and abstract as a whole.

Systems and methods using ultra-low field NMR to detect and identify hazardous materials are needed.

It is therefore an aspect of the embodiments to obtain an NMR measurement by probing a sample with an ultra-low field NMR system. An ultra-low field NMR system has separate prepolarizing and measurement fields. Prepolarizing techniques are used to enhance signal-to-noise. The measurement field is typically less than 1 mT which corresponds to a proton Larmor frequency less than 42 kHz.

It is also an aspect of the embodiments that certain measurement parameters are known. Those measurement parameters include those specifying the sampling temperature, the prepolarizing field, and the measurement field.

It is a further aspect of the embodiments to analyze the NMR measurement to obtain one or more measurement features. T1, T2, T1$\rho$, Larmor frequency, and phase relaxation constant are examples of measurement features that are well known to those practiced in the art the NMR instrumentation.

It is a yet further aspect of the embodiments to compare the measurement features within a database. The database contains the NMR measurement features of materials of interest, such as hazardous materials. For example, a known hydrogen peroxide solution, being a possible explosive precursor, can be examined by a low field NMR system to produce a NMR hazardous material reference for inclusion in the database. If the measurement features obtained from the NMR measurement are similar to the hydrogen peroxide reference then the sample likely contains hydrogen peroxide.

The database can be searched by comparing each NMR hazardous material reference to the measurement features. The measurement features can be expressed as a measurement vector. Similar, each NMR hazardous material reference can be expressed as a reference vector. Correlations, correlation coefficients, and other distance measures or functions can be used for the comparisons. Thresholds can be used to determine if a comparison has identified a material. Those practiced in the arts of classification or pattern recognition are familiar with correlations, distances, vectors, thresholds, and techniques for searching for a matching reference within a database.

BRIEF DESCRIPTION OF THE DRAWINGS

The accompanying figures, in which like reference numerals refer to identical or functionally similar elements throughout the separate views and which are incorporated in and form a part of the specification, further illustrate the present invention and, together with the background of the invention, brief summary of the invention, and detailed description of the invention, serve to explain the principles of the present invention.

DETAILED DESCRIPTION

The particular values and configurations discussed in these non-limiting examples can be varied and are cited merely to illustrate embodiments and are not intended to limit the scope of the invention.

An ultra-low field NMR system can non-invasively examine containers. Database matching techniques can then identify hazardous materials within the containers. Ultra-low field NMR systems are ideal for this purpose because they do not require large powerful magnets and because they can examine materials enclosed in conductive shells and lead shells. The NMR examination technique can be combined with ultra-low field NMR imaging where an NMR image is obtained and analyzed to identify target volumes. Spatial sensitivity encoding techniques can then be used to identify their contents.

Figure 1:
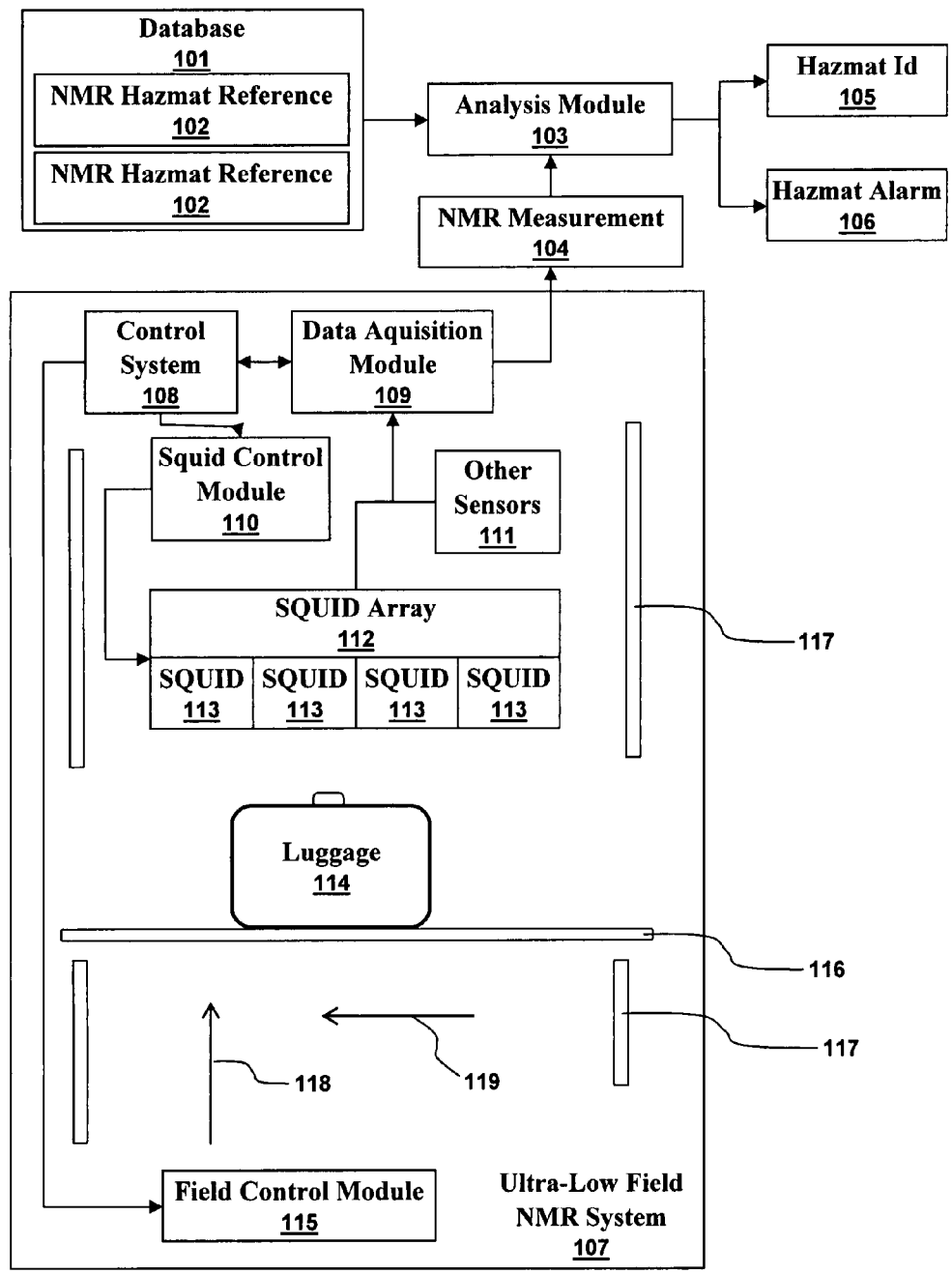
FIG. 1 illustrates a system for examining luggage for hazardous materials in accordance with aspects of the embodiments.

FIG. 1 illustrates a system for examining luggage 114 for hazardous materials in accordance with aspects of the embodiments. Luggage 114 can be conveyed on a carrier 116 through an ultra-low field NMR system 107 on a carrier. A control system 108 controls various aspects and modules of the ultra-low field NMR system 107. A field control module 115 controls the prepolarizing field 118 and the measurement field 119. The SQUID control 110 module controls a SQUID array 112 containing SQUIDs 113. A data acquisition module 109 obtains the SQUID measurements as well as measurements from other sensors 111. The other sensors 111 can measure the sampling temperature of the luggage as well as the strengths and polarities of the magnetic fields.

The data acquisition module 109 can pass an NMR measurement 104 to an analysis module 103 that produces measurement features. The analysis module 103 obtains NMR hazardous material references 102 from a database 101 for comparison to the measurement features. If the comparison indicated that a hazardous material is present, then a hazardous material alarm 106 can alert people to the presence of a hazardous material. The hazardous material identity 105 is the material corresponding to the NMR hazardous material references 102 that matched the measurement features.

As is well known to those practiced in the art of ultra-low field NMR instrumentation, the sensors must often be deactivated while the magnetic prepolarization field 118 is applied. As such, the control system 108 can cause the SQUIDs 113 to deactivate before the prepolarization field is 118 is turned on. The SQUIDs 113 can be reactivated after the prepolarization field 118 is turned off with the measurement field 119 remaining. Magnetic shielding 117 can adjust the ambient field or isolate the ultra-low field NMR system 107 from sources of interference.

A measurement feature can be dependent or independent of the Larmor frequency. The dependence of measurement features on Larmor frequency can be used for further identification of the material. Additionally, a dependent measurement feature can be made to be independent of the Larmor frequency by mathematically removing or normalizing its effect. Those practiced in the arts of NMR or MRI are familiar with compensating measurement features for their dependence on the Larmor frequency.

Figure 2:
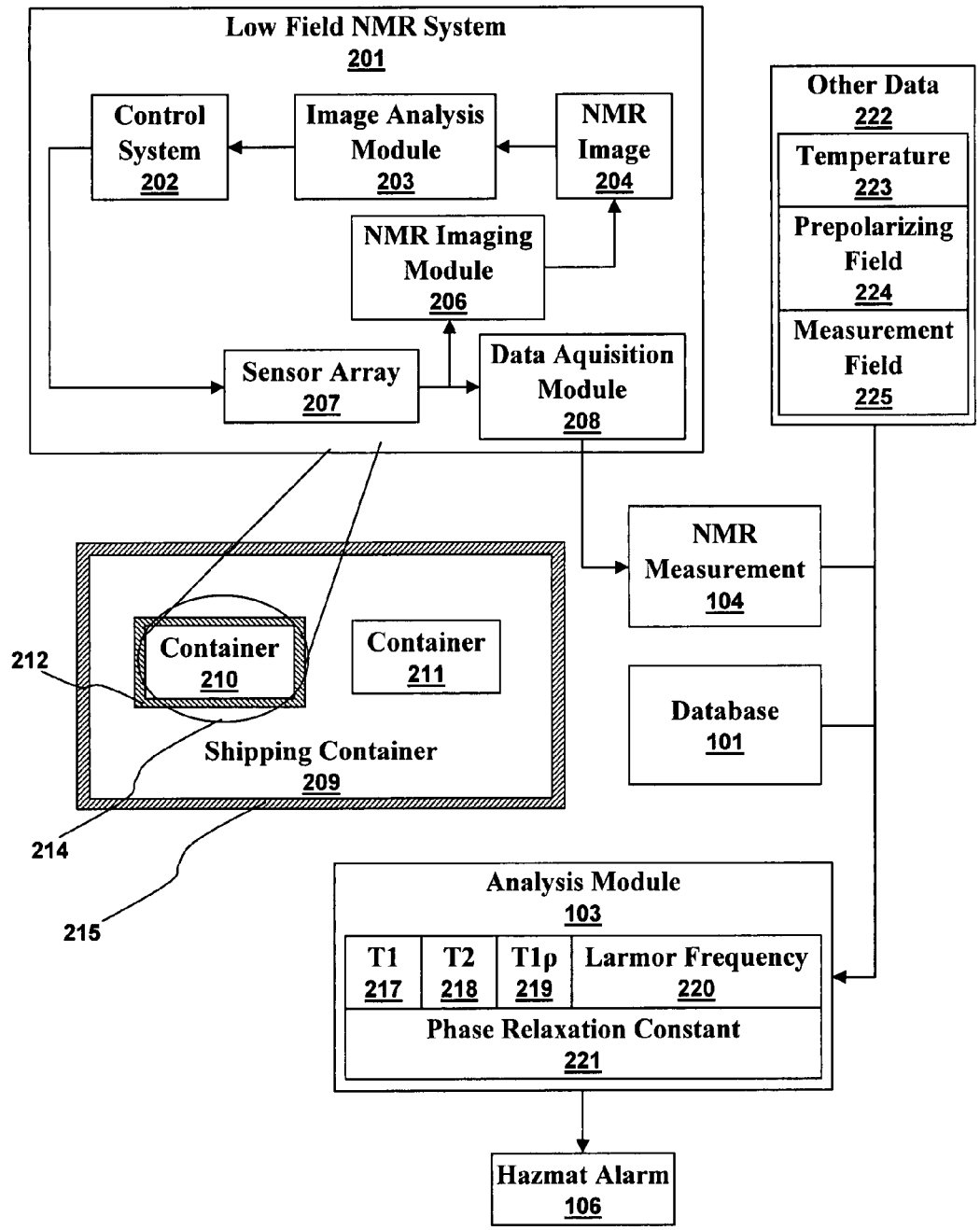
FIG. 2 illustrates a system for imaging shipping container contents while examining it for hazardous materials in accordance with aspects of the embodiments.

FIG. 2 illustrates a system for imaging shipping container contents while examining it for hazardous materials in accordance with aspects of the embodiments. A shipping container 209 can contain smaller containers 210, 211. For example, luggage can contain a tube of tooth paste. The shipping container 209 can have a conductive shell 215, for example lead or aluminum. A container 210 can also have a conductive shell 212.

An ultra-low filed NMR system 201 can examine the shipping container 208 by first imaging its contents. Imaging can be achieved by spatially varying the prepolarizing or measurement fields. For clarity, the magnetic fields and field control elements are not presented in FIG. 2. One can also use the spatial distribution of sensitivity of each magnetic field sensor channel to distinguish the contents. The control system 202 controls the sensor array 207. The sensor array 207 contains magnetic field sensors such as the SQUIDs of FIG. 1. Those practiced in the arts of NMR or MRI are familiar with using spatial sensitivity coding and with using the spatial dependence of the prepolarizing and measurement fields to produce images.

The NMR imaging module 206 constructs an NMR image 204 from the output of the sensor array 207. An image analysis module 203 can examine the NMR image 204 to identify target volumes inside the shipping container 209. As illustrated in FIG. 2, the image analysis module has identified a container 210 has needing a closer look. A target volume 214 containing the container 210 is identified.

The NMR image 204 is an interior image of the shipping container 209. Other imaging devices, such as an X-ray scanner, can also produce interior images. Regardless of the source, an interior image is analyzed to identify target volumes. The other imaging device can be inside or outside of the low field NMR system 201. Most importantly, however, the low field NMR system 201 can simultaneously act as both an imaging device and as a component of a hazardous material detection system by NMR measurement of material properties as described for FIG. 1.

The data acquisition module 208 produces an NMR measurement from the sensor array output. The analysis module 103 obtains the NMR measurement 104 as well as other data 222 that can include sampling temperature 223, prepolarizing field parameters 224, and measurement field parameters 225. Magnetic field parameters can include polarity and strength. The analysis module can produce measurement features such as T1 217, T2 218, T1ρ 219, Larmor frequency 220, and phase relaxation constant 221. Comparing the measurement features to the contents of a database 101 can result in a hazardous material alarm 106.

Figure 3:
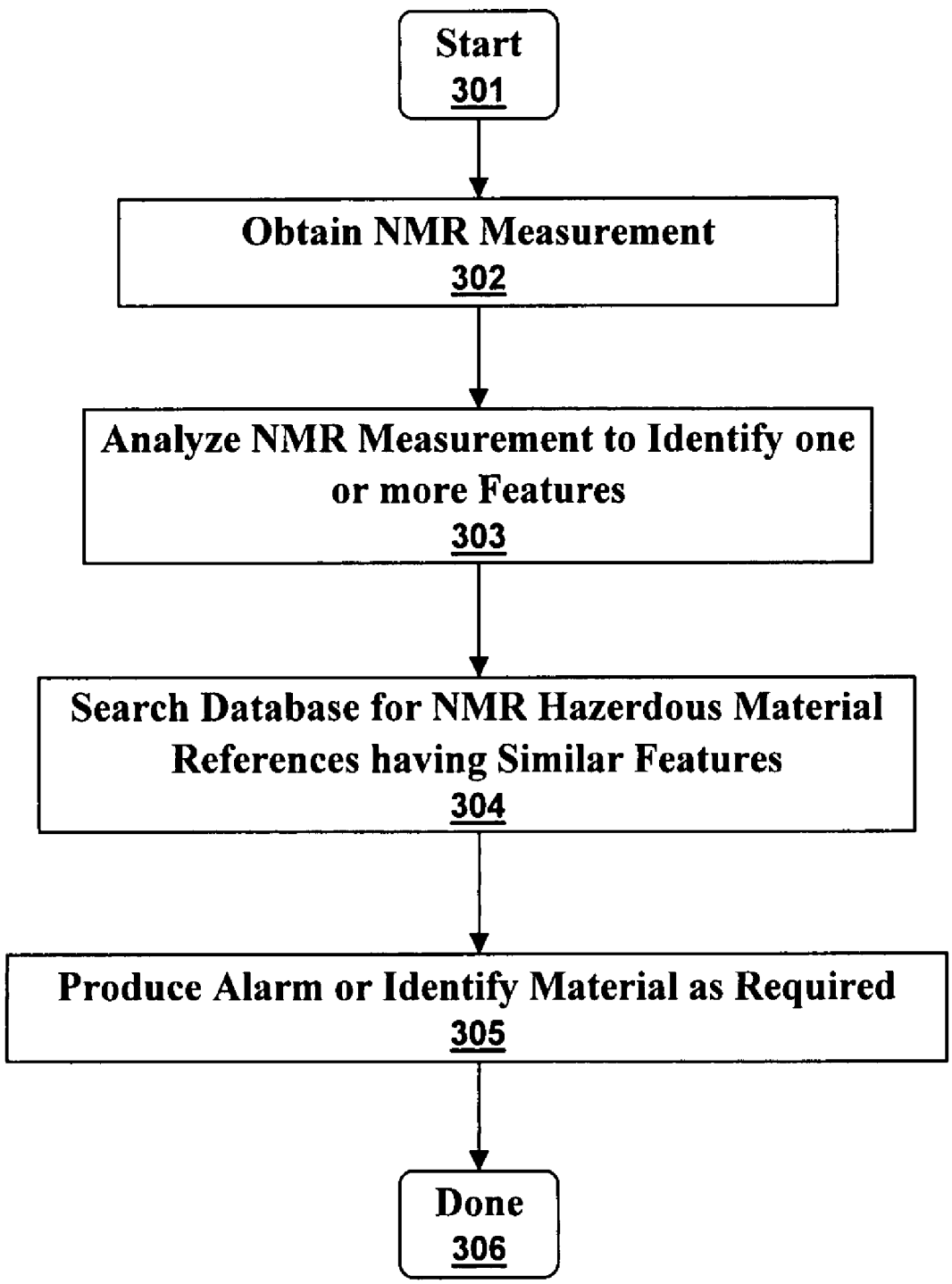
FIG. 3 illustrates a high level flow diagram of identifying hazardous materials in accordance with aspects of some embodiments.

FIG. 3 illustrates a high level flow diagram of identifying hazardous materials in accordance with aspects of some embodiments. After the start 301, an NMR measurement is obtained 302 and analyzed to identify NMR measurement features 303. Next, a database is searched for NMR hazardous material references that are similar to the NMR measurement features 305. If a hazardous material is indicated, an alarm can be activated and the material can be identified 305 before the process is complete 306.

Figure 4:
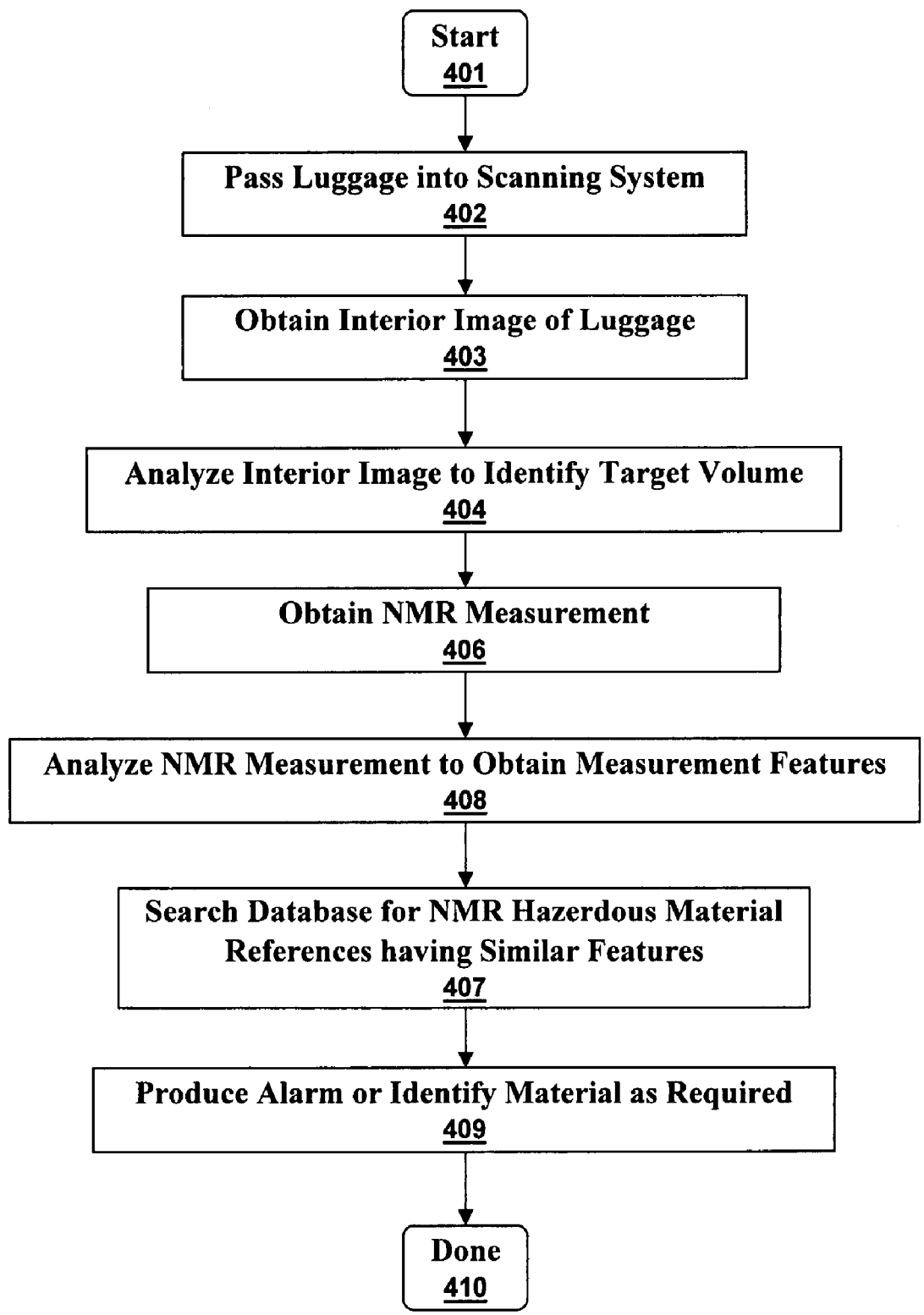
FIG. 4 illustrates a high level flow diagram of locating target volumes and identifying hazardous materials in accordance with aspects of some embodiments.

FIG. 4 illustrates a high level flow diagram of locating target volumes and identifying hazardous materials in accordance with aspects of some embodiments. After the start 401, luggage is passed into the scanning system 402 and an interior image of the luggage produced 403. The interior image can be analyzed to identify a target volume 404. An NMR measurement can be obtained 406 and analyzed to produce NMR measurement features 408. A database can then be searched for references similar to the NMR measurement features 407 and an alarm produced and the material identified if a matching reference is found in the database 409. Finally the process is done 410.

Embodiments can be implemented in the context of modules. In the computer programming arts, a module (e.g., a software module) can be implemented as a collection of routines, data structures, firmware and hardware that perform particular tasks or implement a particular algorithm, function, capability, or abstract data type.

The examples discussed above are intended to illustrate aspects of the embodiments. The phrases "an embodiment", "some embodiments", or "certain embodiments" do not necessarily refer to the same embodiment or any specific embodiment.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A method comprising:
obtaining an NMR measurement from a sample wherein an ultra-low field NMR system probes the sample and produces the NMR measurement, wherein a sampling temperature, prepolarizing magnetic field, and measurement magnetic field are known and wherein the prepolarizing magnetic field and the measurement magnetic field are different;
analyzing the NMR measurement to obtain at least one measurement feature wherein the measurement feature comprises T1, T2, or T1ρ;
searching for the at least one measurement feature within a database comprising at least one NMR hazardous material reference to determine if the sample comprises a hazardous material.

2. The method of claim 1 wherein the measurement features are obtained as a function of Larmor frequency.

3. The method of claim 1 wherein the measurement feature comprises a phase relaxation constant.

4. The system of claim 1 wherein the sample is encased in a conductive shell.

5. A method comprising:
measuring a sampling temperature;
obtaining an NMR measurement and an interior image from a sample wherein an ultra-low field NMR system probes the sample and produces the NMR measurement, wherein a prepolarizing magnetic field and measurement magnetic field are known and wherein the prepolarizing magnetic field and the measurement magnetic field are different;
analyzing the NMR measurement to obtain at least one measurement feature;
searching for the at least one measurement feature within a reference library comprising at least one NMR hazardous material reference to determine if the sample comprises a hazardous material.

6. The method of claim 5 wherein the interior image is an NMR image produced by the ultra-low field NMR system.

7. The method of claim 5 wherein the ultra-low field NMR system comprises a magnetic sensor array and a means for providing an image of the target volume within the sample comprising spatial sensitivity encoding, and wherein the NMR measurement corresponds to a composition within a target volume within the sample and identified from analysis of the interior image.

8. The method of claim 5 further comprising identifying a target volume from the interior image, wherein the ultra-low field NMR system comprises a magnetic sensor array, wherein the spatial dependence of the prepolarizing magnetic field and the measurement magnetic field are used to produce an image of the target volume, and wherein the NMR measurement corresponds to a composition within the target volume.

9. A method comprising:
passing an container through a scanning system comprising an ultra-low field NMR system wherein the container is unopened, wherein the ultra-low field NMR system probes the container and produces an NMR measurement, wherein a sampling temperature, prepolarizing magnetic field, and measurement magnetic field are known and wherein the prepolarizing magnetic field and the measurement magnetic field are different;
analyzing the NMR measurement to obtain at least one measurement feature;
searching for the at least one measurement feature within a database comprising at least one NMR hazardous material reference to determine if the sample comprises a hazardous material.

10. The method of claim 9 wherein the container is luggage.

11. The method of claim 9 wherein the container is a shipping container.

12. The method of claim 9 wherein the container comprises a conductive shell.

13. The method of claim 9 wherein the container contains smaller containers comprising conductive shells.

14. The method of claim 9 further comprising obtaining an interior image of the container wherein the scanning system further comprises an interior imaging system.

15. The method of claim 14 wherein the interior imaging system and the ultra-low field NMR system are the same system.

16. The method of claim 15 further comprising examining the interior image to identify a target volume within the container, wherein the ultra-low field NMR system comprises a magnetic sensor array, and wherein the NMR measurement corresponds to a composition within the target volume.

17. The method of claim 16 wherein the at least one measurement feature comprises T1.

18. The method of claim 14 wherein the interior imaging system is not an NMR system.

19. The method of claim 18 further comprising examining the interior image to identify a target volume within the container, wherein the ultra-low field NMR system comprises a magnetic sensor array, and wherein the NMR measurement corresponds to a composition within the target volume.

* * * * *